United States Patent
Shinohara et al.

(10) Patent No.: US 7,557,093 B2
(45) Date of Patent: Jul. 7, 2009

(54) COMPOSITION FOR PROMOTING COLLAGEN PRODUCTION

(75) Inventors: Shigeo Shinohara, Kyoto (JP); Mitsuaki Kawamura, Kyoto (JP)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 10/574,696

(22) PCT Filed: Oct. 8, 2004

(86) PCT No.: PCT/JP2004/015298
§ 371 (c)(1), (2), (4) Date: Dec. 4, 2006

(87) PCT Pub. No.: WO2005/034902
PCT Pub. Date: Apr. 21, 2005

(65) Prior Publication Data
US 2007/0135374 A1    Jun. 14, 2007

(30) Foreign Application Priority Data
Oct. 8, 2003   (JP) ............................. 2003-349156

(51) Int. Cl.
A61K 31/70    (2006.01)
A01N 43/04    (2006.01)

(52) U.S. Cl. ............................. 514/47; 514/43; 514/45; 514/46; 514/48; 514/49; 514/50; 514/51

(58) Field of Classification Search ....................... None
See application file for complete search history.

(56) References Cited

U.S. PATENT DOCUMENTS

| | | | |
|---|---|---|---|
| 4,544,559 | A | 10/1985 | Gil et al. |
| 5,053,230 | A | 10/1991 | Gazzani |
| 5,182,269 | A | 1/1993 | Gazzani |
| 5,602,109 | A | 2/1997 | Masor et al. |
| 6,203,805 | B1 | 3/2001 | Collins et al. |
| 2002/0141955 | A1 | 10/2002 | Zimmerman et al. |
| 2003/0068349 | A1 | 4/2003 | Jentzsch et al. |
| 2004/0116373 | A1 | 6/2004 | Okuda et al. |

FOREIGN PATENT DOCUMENTS

| | | |
|---|---|---|
| EP | 0256472 | 2/1988 |
| EP | 0 036 882 | 4/1990 |
| JP | 63-183535 | 7/1988 |
| JP | 6-48934 | 2/1994 |
| JP | 9-295915 | 11/1997 |
| JP | 2001-31549 | 2/2001 |
| JP | 2003-40729 | 2/2003 |
| JP | 2001-278783 | 10/2003 |
| JP | 2001-316240 | 11/2003 |
| WO | WO 98/32429 | 7/1998 |

OTHER PUBLICATIONS

L.J. Croucher, et al., 'Extracellular ATP and UTP stimulate cartilage proteoglycan and collagen accumulation in bovine articular chondrocyte pellet cultures,' *Biochimica et Biophysica Acta* 1502:297-306 (2000).
Translation of International Preliminary Report on Patentability of International Application PCT/JP2004/01528, filed Oct. 8, 2004.
Amendment After Final filed Jan. 8, 2009, in U.S. Appl. No. 10/510,738.
International Search Report of International Application PCt/JP03/04247, filed Apr. 3, 2003.
Office Action mailed Aug. 7, 2007, in U.S. Appl. No. 10/510,738.
Office Action mailed Jul. 8, 2008, in U.S. Appl. No. 10/510,738.
Office Action mailed Oct. 4, 2007, in U.S. Appl. No. 10/510,738.
Reply to Office Action filed Apr. 3, 2008, in U.S. Appl. No. 10/510,738.
Thellung, S. et al., "Polydeoxyribonucleotides Enhance the Proliferation of Human Skin Fibroblasts: Involvement of $A_2$ Purinergic Receptor Subtypes," *Life Sci.* 64:1661-74 (1999).
Office Action mailed Mar. 31, 2009, in U.S. Appl. No. 10/510,738.

*Primary Examiner*—Patrick T Lewis
(74) *Attorney, Agent, or Firm*—Finnegan, Henderson, Farabow, Garrett & Dunner, L.L.P.

(57) ABSTRACT

The invention provides a composition for promoting collagen production, and more specifically, provides a composition capable of promoting collagen production in human dermis. Further, the invention provides a method for promoting collagen production. The invention provides a composition for promoting collagen production containing a purine nucleic acid-related substance as an active ingredient as well as a composition for promoting collagen production containing a purine nucleic acid-related substance and a pyrimidine nucleic acid-related substance. The method for promoting collagen production of the invention comprises applying a purine nucleic acid-related substance alone or in combination with a pyrimidine nucleic acid-related substance to the skin.

8 Claims, 1 Drawing Sheet

AMP concentrations of culture media (w/v %)

COMPOSITION FOR PROMOTING COLLAGEN PRODUCTION

TECHNICAL FIELD

The present invention relates to a composition for promoting collagen production. The invention also relates to a method for promoting collagen production in the dermis.

BACKGROUND OF THE INVENTION

About 90% of the dermis of the skin is collagen, which exhibits the functions of supporting the skin structure, providing an environment for cell survival, and retaining moisture. It is known that collagen is lost when the skin is subject to specific exogenous influences, such as ultraviolet-ray exposure, dryness, etc. It has been found that collagen is lost by aging and stress. It has also been found that such exogenous influences and/or aging causes a reduction in the amount of collagen production in skin fibroblast.

The functions of retaining a moderate amount of collagen as well as exhibiting an excellent collagen production ability are important in maintaining healthy skin. Heretofore, substances that promote collagen production have been actively sought (e.g., Japanese Unexamined Patent Publication Nos. 2001-316240 and 2003-278783,A). However, it has not been reported that nucleic acid and its related substances have an action of promoting collagen production.

SUMMARY OF THE INVENTION

The invention aims to provide a composition for promoting collagen production, and more specifically, to provide a composition capable of promoting collagen production in human dermis. Further, the invention aims to apply the above-described composition for promoting collagen production to external preparations.

The present inventors carried out extensive research to achieve the above-described objects, and found that purine nucleic acid-related substances, especially adenosine 5'-monophosphate, and salts thereof, have an action of promoting collagen production in the dermis. Moreover, the inventors found that a pyrimidine nucleic acid-related substance has an effect of potentiating the collagen production promoting action of the purine nucleic acid-related substance.

More specifically, the present invention relates to the following compositions for promoting collagen production.

Item 1. A composition for promoting collagen production, comprising a purine nucleic acid-related substance.

Item 2. A composition for promoting collagen production according to Item 1, further comprising a pyrimidine nucleic acid-related substance.

Item 3. A composition for promoting collagen production according to Item 1, wherein the purine nucleic acid-related substance is at least one member selected from the group consisting of adenine, adenosine, adenosine phosphate, a metabolite of adenosine phosphate, and a salt thereof.

Item 4. A composition for promoting collagen production according to Item 1, wherein the purine nucleic acid-related substance is at least one member selected from the group consisting of adenosine monophosphate and a salt thereof.

Item 5. A composition for promoting collagen production according to Item 1, wherein the purine nucleic acid-related substance is at least one member selected from the group consisting of adenosine 5'-monophosphate and a salt thereof.

Item 6. A composition for promoting collagen production according to Item 2, wherein the pyrimidine nucleic acid-related substance is at least one member selected from the group consisting of uracil, uridine, uridine phosphate, and a salt thereof.

Item 7. A composition for promoting collagen production according to Item 2, wherein the pyrimidine nucleic acid-related substance is at least one member selected from the group consisting of uridine monophosphate and a salt thereof.

Item 8. A composition for promoting collagen production according to Item 2, wherein the pyrimidine nucleic acid-related substance is at least one member selected from the group consisting of uridine 5'-monophosphate and a salt thereof.

Item 9. A composition for promoting collagen production according to Item 2, wherein the purine nucleic acid-related substance is at least one member selected from the group consisting of adenine, adenosine, adenosine phosphate, a metabolite of adenosine phosphate, and a salt thereof and the pyrimidine nucleic acid-related substance is at least one member selected from the group consisting of uracil, uridine, uridine phosphate, and a salt thereof.

Item 10. A composition for promoting collagen production according to Item 2, wherein the purine nucleic acid-related substance is selected from the group consisting of adenosine monophosphate and a salt thereof and the pyrimidine nucleic acid-related substance is at least one member selected from the group consisting of uridine monophosphate and a salt thereof.

Item 11. A composition for promoting collagen production according to Item 2, wherein the purine nucleic acid-related substance is selected from the group consisting of adenosine 5'-monophosphate and a salt thereof and the pyrimidine nucleic acid-related substance is at least one member selected from the group consisting of uridine 5'-monophosphate and a salt thereof.

Item 12. A composition for promoting collagen production according to Item 2, wherein the composition contains the pyrimidine nucleic acid-related substance in a proportion of 0.001 to 100 parts by weight per part by weight of the purine nucleic acid-related substance.

Item 13. A composition for promoting collagen production according to Item 1, wherein the composition contains the purine nucleic acid-related substance in a proportion of 0.01 to 10% by weight based on the total amount of the composition.

Item 14. A composition for promoting collagen production according to Item 1, wherein the composition contains the pyrimidine nucleic acid-related substance in a proportion of 0.0001 to 10% by weight based on the total amount of the composition.

Item 15. A composition for promoting collagen production according to Item 1 used for a cosmetic, or an externally-applied medical or quasi-medical drug.

Item 16. A composition for promoting collagen production according to Item 1 used for a cosmetic.

The invention also relates to the following methods for promoting collagen production.

Item 17. A method for promoting collagen production, comprising applying to the skin a purine nucleic acid-related substance.

Item 18. A method for promoting collagen production according to Item 17, comprising applying to the skin a purine nucleic acid-related substance in combination with a pyrimidine nucleic acid-related substance.

Item 19. A method for promoting collagen production according to Item 17, comprising applying to the skin an externally-applied composition containing the purine nucleic acid-related substance.

Item 20. A method for promoting collagen production according to Item 18, comprising applying to the skin an externally-applied composition containing the purine nucleic acid-related substance and the pyrimidine nucleic acid-related substance.

Item 21. A method for promoting collagen production according to Item 17, wherein the purine nucleic acid-related substance is at least one member selected from the group consisting of adenine, adenosine, adenosine phosphate, a metabolite of adenosine phosphate, and a salt thereof.

Item 22. A method for promoting collagen production according to Item 17, wherein the purine nucleic acid-related substance is at least one member selected from the group consisting of adenosine monophosphate and a salt thereof.

Item 23. A method for promoting collagen production according to Item 17, wherein the purine nucleic acid-related substance is selected from the group consisting of adenosine 5'-monophosphate and a salt thereof.

Item 24. A method for promoting collagen production according to Item 18, wherein the pyrimidine nucleic acid-related substance is at least one member selected from the group consisting of uracil, uridine, uridine phosphate, and a salt thereof.

Item 25. A method for promoting collagen production according to Item 18, wherein the pyrimidine nucleic acid-related substance is at least one member selected from the group consisting of uridine monophosphate and a salt thereof.

Item 26. A method for promoting collagen production according to Item 18, wherein the pyrimidine nucleic acid-related substance is at least one member selected from the group consisting of uridine 5'-monophosphate and a salt thereof.

Item 27. A method for promoting collagen production according to Item 18, wherein the purine nucleic acid-related substance is at least one member selected from the group consisting of adenine, adenosine, adenosine phosphate, a metabolite of adenosine phosphate, and a salt thereof and the pyrimidine nucleic acid-related substance is at least one member selected from the group consisting of uracil, uridine, uridine phosphate, and a salt thereof.

Item 28. A method for promoting collagen production according to Item 18, wherein the purine nucleic acid-related substance is selected from the group consisting of adenosine monophosphate and a salt thereof and the pyrimidine nucleic acid-related substance is at least one member selected from the group consisting of uridine monophosphate and a salt thereof.

Item 29. A method for promoting collagen production according to Item 18, wherein the purine nucleic acid-related substance is selected from the group consisting of adenosine 5'-monophosphate and a salt thereof and the pyrimidine nucleic acid-related substance is at least one member selected from the group consisting of uridine 5'-monophosphate and a salt thereof.

Item 30. A method for promoting collagen production according to Item 18, wherein the composition contains the pyrimidine nucleic acid-related substance in a proportion of 0.001 to 100 parts by weight per part by weight of the purine nucleic acid-related substance.

Item 31. A method for promoting collagen production according to Item 19, wherein the externally-applied composition contains the purine nucleic acid-related substance in a proportion of 0.01 to 10% by weight based on the total amount of the composition.

Item 32. A method for promoting collagen production according to Item 20, wherein the externally-applied composition contains the pyrimidine nucleic acid-related substance in a proportion of 0.0001 to 10% by weight based on the total amount of the composition.

Item 33. A method for promoting collagen production according to Item 19, wherein the externally-applied composition is used for a cosmetic, or an externally-applied medical or quasi-medical drug.

Item 34. A method for promoting collagen production according to Item 19, wherein the externally-applied composition is used for a cosmetic.

Item 35. A method for promoting collagen production according to Item 17, comprising applying to the skin the composition for promoting collagen production of Item 1.

Item 36. A method for promoting collagen production according to Item 18, comprising applying to the skin the composition for promoting collagen production of Item 2.

Further, the invention also relates to uses of the following aspects.

Item 37. Use of a purine nucleic acid-related substance for preparation of a composition for promoting collagen production.

Item 38. Use of a purine nucleic acid-related substance and a pyrimidine nucleic acid-related substance for preparation of a composition for promoting collagen production.

Item 39. Use of a purine nucleic acid-related substance for collagen production.

Item 40. Use of a purine nucleic acid-related substance and a pyrimidine nucleic acid-related substance for collagen production.

Figure 1:
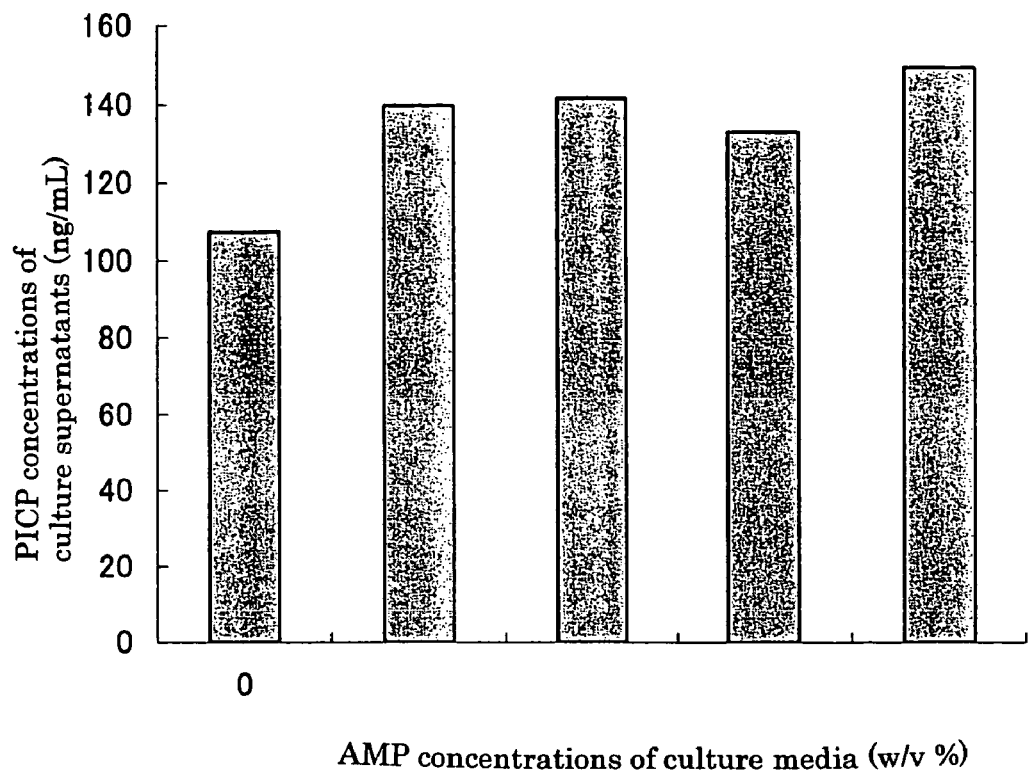
FIG. 1 is a chart showing the PICP concentration produced when the human skin fibroblasts were cultured in media containing various concentrations of AMP2Na in Test Example 1.

BEST MODE FOR CARRYING OUT THE INVENTION (I) Composition for Promoting Collagen Production The composition for promoting collagen production of the invention comprises a purine nucleic acid-related substance as an active ingredient. The "purine nucleic acid-related substance" used herein refers to purine, various purine derivatives having a purine skeleton, and salts thereof.

There is no limitation on the purine nucleic acid-related substances usable in the invention insofar as the purine nucleic acid-related substance can be mixed in cosmetics, externally-applied medical/quasi-medical drugs. Those that are water soluble or hydrophilic are preferable. In general, examples of such purine nucleic acid-related substances include adenine nucleic acid-related substances such as adenine, adenosine, adenosine phosphates(for example, adenosine 2'-phosphate, adenosine 3'-phosphate, adenosine 5'-phosphate, adenosine 5'-diphosphate, adenosine 5'-triphosphate, cyclic adenosine phosphate, adenylosuccinic acid, nicotinamide adenine monodinucleotide (NMN), nicotinamide adenine dinucleotide (NAD), nicotinamide adenine dinucleotide phosphate (NADP), flavin adenine dinucleotide (FAD), etc.), metabolites thereof (for example, hypoxanthine, inosine, inosinic acid, etc.), and salts thereof; and guanine nucleic acid-related substances such as guanine, guanosine, guanosine phosphates (for example, guanosine 3'-phosphate, guanosine 5'-phosphate, guanosine 5'-diphosphate and guanosine 5'-triphosphate, etc.), metabolites thereof (for example, xanthylic acid, xanthin, etc.), and salts thereof.

Among them, preferable examples of the purine nucleic acid-related substance in the invention include the above-mentioned adenine nucleic acid-related substances. More preferable among these are adenosine phosphates, metabolites thereof, and salts thereof, and particularly preferable are adenosine phosphates and salts thereof. Among adenosine phosphates, adenosine 2'-phosphate, adenosine 3'-phosphate, adenosine 5'-phosphate (AMP) can be suitably used, and adenosine 5'-phosphate (AMP) is particularly preferable.

Examples of such salts include alkali metal salts, such as sodium salts, potassium salts, etc.; alkaline earth metal salts, such as calcium salts, magnesium salts, barium salts, etc.; basic amino acid salts, such as arginine, lysine, etc.; ammonium salts, such as ammonium salts, tricyclohexylammonium salts, etc.; various kinds of alkanolamine salts, such as monoethanolamine salts, diethanolamine salts, triethanolamine salts, monoisopropanolamine salts, diisopropanolamine salts, and triisopropanolamine salts, etc.; etc. Preferable among these are alkali metal salts, such as sodium salts, etc. Specific examples of alkali metal salts include adenosine monophosphate monosodium and adenosine monophosphate disodium.

Such purine nucleic acid-related substances may be used alone or in combination of two or more such species as an active ingredient(s) of the composition for promoting collagen production of the invention.

The proportion of purine nucleic acid-related substance usable in the composition for promoting collagen production of the invention varies depending on the type of purine nucleic acid-related substance, existence and type of the pyrimidine nucleic acid-related substance described later, intended use and/or shape of the composition, etc., but is usually suitably adjusted within the range 0.01 to 10% by weight, preferably 1 to 10% by weight, and more preferably 3 to 6% by weight.

Preferably, the composition for promoting collagen production of the invention comprises, in addition to the above-described purine nucleic acid-related substance, a pyrimidine nucleic acid-related substance. The combined use thereof can further enhance the action of promoting collagen production of the purine nucleic acid-related substance. The "pyrimidine nucleic acid-related substance" used herein refers to pyrimidine, various pyrimidine derivatives having a pyrimidine skeleton, and salts thereof.

There is no limitation on the pyrimidine nucleic acid-related substances usable in the composition for promoting collagen production of the invention insofar as the pyrimidine nucleic acid-related substance can be mixed in cosmetics, externally-applied medical/quasi-medical drugs. Those that are water soluble or hydrophilic are preferable. Examples of such pyrimidine nucleic acid-related substances include uracil nucleic acid-related substances, such as uracil, uridine, uridine phosphates [uridine monophosphates (uridine 5'-phosphate, uridine 3'-phosphate, and uridine 2'-phosphate), uridine diphosphates, uridine triphosphates, cyclic uridine phosphate, etc.], deoxyuridine, deoxyuridine phosphates [5'-deoxyuridine diphosphate (dUDP), 5'-deoxyuridine phosphate(dUMP), etc.], and salts thereof; cytosine nucleic acid-related substances, such as cytosine, cytidine, cytidine phosphates (CMP) [cytidine monophosphates (cytidine 5'-phosphate, cytidine 3'-phosphate, cytidine 2'-phosphate), cytidine triphosphate (CTP), cytidine diphosphate (CDP)], deoxycytidine, deoxycytidine phosphates (5'-deoxycytidine triphosphate (dCTP), 5'-deoxycytidine diphosphate (dCDP), 5'-deoxycytidine phosphate (dCMP), etc.) and salts thereof; and thymine nucleic acid related-substances, such as thymine, thymidine, thymidine phosphates [thymidine monophosphates (dTMP), thymidine diphosphates (dTDP), thymidine triphosphates (dTTP), etc.], orotic acid, orotidine 5'-phosphate, and salts thereof.

Any pyrimidine nucleic acid-related substances are usable irrespective of purity insofar as each such component is contained. Usable as pyrimidine nucleic acid-related substances are plant extracts containing each such component, such as Brassicaceae plant extracts (especially, seed extracts), Leguminosae plant extracts, etc.

The above-mentioned uracil nucleic acid-related substances are preferably used as the pyrimidine nucleic acid-related substances because they can further effectively enhance the action of promoting collagen production of the purine nucleic acid-related substance. Preferable among the above are uridine, uridine phosphates, and salts thereof, with uridine phosphates and salts thereof being more preferable. It is preferable to use uridine monophosphate, especially uridine 5'-phosphate (UMP), as the uridine phosphate.

Examples of the above-mentioned salts include sodium salts, potassium salts, and like alkali metal salts; calcium salts, magnesium salts, barium salts, and like alkaline earth metal salts; arginine, lysine, and like basic amino acid salts; ammonium salts, tricyclohexylammonium salts, and like ammonium salts; a wide variety of alkanolamine salts, such as monoethanolamine salts, diethanolamine salts, triethanolamine salts, monoisopropanolamine salts, diisopropanolamine salts, triisopropanolamine salts, etc.; etc.

Preferable among these are alkali metal salts such as sodium salts. Specific examples of alkali metal salts include uridine monophosphate monosodium and uridine monophosphate disodium.

Such a pyrimidine nucleic acid-related substance may be used alone or in combination of two or more such species for the composition for promoting collagen production of the present invention.

There is no limitation on the proportion of pyrimidine nucleic acid-related substance usable in the composition for promoting collagen production of the invention insofar as the effect of potentiating the collagen production can be demonstrated. For example, the proportion of pyrimidine nucleic acid-related substance is suitably adjusted within the range of 0.001 to 100 parts by weight per part by weight of purine nucleic acid-related substance contained in the composition. The proportion of pyrimidine nucleic acid-related substance is preferably within the range of 0.01 to 100 parts by weight, more preferably 0.01 to 10 parts by weight, and still more preferably 0.01 to 1 part by weight, per part by weight of purine nucleic acid-related substance. The proportion of the pyrimidine nucleic acid-related substance based on the total amount of the composition for promoting collagen production is, for example, 0.0001 to 10% by weight, preferably 0.0001 to 1% by weight, and more preferably 0.0001 to 0.1% by weight.

The composition for promoting collagen production can be formed into various shapes by the combined use of the above-described ingredients with cosmetically or pharmaceutically acceptable bases, carriers and/or additives. Known cosmetically or pharmaceutically acceptable bases, carriers and/or additives can be used. The composition for promoting collagen production of the invention can comprise, if required, a wide variety of known components used in externally-applied compositions suitable for the skin and/or mucosa, such as cosmetics and externally-applied medical/quasi-medical drugs. Examples of such components include surfactants, colorants (dyes, pigments), flavors, antiseptics, bactericides (antibacterials), thickeners, antioxidants, sequestering agents, refrigerants, deodorizers humectants, UV absorbers, UV dispersants, vitamins, plant extracts, astringents, anti-inflammatory agents (antiphlogistic agents), whiteners, cell activators, vasodilators, blood circulation accelerators, skin function accelerators, and the like.

Examples of the above-mentioned components include anionic surfactants, such as salts of higher fatty acids, alkylsulfonate salts, polyoxyethylene alkyl ether sulfates, alkyl ether phosphates, N-acylamino acid salts, acyl N-methyl taurine salts, etc.; cationic surfactants, such as alkyltrimethylammonium chlorides, dialkyldimethylammonium chlorides, etc.; amphoteric surfactants, such as alkyldimethylaminoacetate betaines, alkylamidedimethylaminoacetate betaines, 2-alkyl-N-carboxy-N-hydroxyimidazolinium betaines, etc.; nonionic surfactants, such as polyoxyethylene bases, polyhydric alcohol ester bases, ethylene oxide/propylene oxide block copolymers, etc. Any high molecular weight surfactants or natural surfactants can also be used without limitation.

Examples of antiseptics include ethyl p-hydroxybenzoate, salicylic acid, sorbic acid, etc. Examples of thickeners include xanthane gum, carboxymethyl cellulose sodium, carboxy vinyl polymers, etc. Examples of sequestering agents include sodium salts of ethylenediamine tetra acetic acid, phosphoric acid, citric acid, etc.

The composition for promoting collagen production of the invention is used as an externally-applied preparation to be spread or sprayed to the skin. More specifically, the composition for promoting collagen production of the invention can be widely used as cosmetics or externally-applied medical/quasi-medical drugs (dermatological preparations). Preferable among the above are cosmetics given that cosmetics can promote collagen production in the skin on a daily basis. Examples of such externally-applied agents include a wide variety of hair care products such as hair restorers and hair growth agents, as well as, shampoos, rinses, and hair lotions (including tonics and liquids) that have hair restoration and/or hair growth effects.

The composition for promoting collagen production of the invention can take any form without limitation insofar as it is applicable to the skin or mucosa. Examples of form include pastes, mousses, gels, liquids, emulsions, suspensions, creams, ointments, sheets, aerosols, sprays, and liniments. Examples of cosmetics include lotions; emollient emulsions, milky lotions, nourishing emulsions, cleansing emulsions, and like emulsions; emollient creams, massage creams, cleansing creams, makeup creams, and like creams; etc. Examples of hair care products include hair tonics, hair creams, hair lotions, aerosols (air sprays), mousses, shampoos, rinses, liquids, etc.

The composition for promoting collagen production of the invention can be directly applied to or sprayed onto the skin or mucosa as a cosmetic or an externally-applied medical/quasi-medical drug. The composition can be applied to the skin or mucosa once to 5 or 6 times per day in an amount effective to promote collagen production according to the age of the user (human), the gender, the intended use, the condition of the affected part of the skin, etc.

The composition for promoting collagen production of the invention promotes collagen production, and therefore exhibits the effects of anti-aging, moisturizing, anti-acne, anti-wrinkle, anti-sagging, anti-dullness, hair growth, anti-dandruff, nail beautifying, wound healing, etc. Thus, the composition for promoting collagen production of the invention can be used as a cosmetic or an externally-applied medical/quasi-medical drug for the purpose of anti-aging, moisturizing, anti-acne, anti-wrinkle, anti-sagging, anti-dullness, hair growth, anti-dandruff, nail beautifying, wound healing, etc. Among the above, the composition for promoting collagen production of the invention is advantageously useful for externally-applied preparations for the purpose of anti-aging, moisturizing, anti-acne, anti-wrinkle, anti-sagging, anti-dullness, hair growth, anti-dandruff, nail beautifying, wound healing, etc. In particular, the composition for promoting collagen production of the invention is useful for various externally-applied preparations for the purpose of anti-wrinkle.

The composition for promoting collagen production of the invention demonstrates an excellent collagen-production promotion effect when applied to the skin. Accordingly, the invention provides use of a purine nucleic acid-related substance for the preparation of compositions for promoting collagen production; and use of a purine nucleic acid-related substance and a pyrimidine nucleic acid-related substance for the preparation of compositions for promoting collagen production.

(II) Method for Promoting Collagen Production

The present invention also provides a method for promoting collagen production. The method is carried out by applying a purine nucleic acid-related substance to the skin.

In the method of the invention, by applying a pyrimidine nucleic acid-related substance and a purine nucleic acid-related substance to the skin, the collagen-production promotion effect becomes more prominent.

According to the method of the invention, the application of the substance(s) to the skin can be achieved by spreading, spraying, or sticking of the composition for promoting collagen production (I) above to the skin.

In the method of the invention, there is no limitation on the frequencies with which a purine nucleic acid-related substance alone or a combination of a purine nucleic acid-related substance and a pyrimidine nucleic acid-related substance is applied to the skin or the like and also the application amounts thereof are not limited. For example, either or both of the substances are applied to the skin in an appropriate amount one to five or six times per day according to the age of the application target, the gender, the intended use, the condition of the affected part of the skin, etc. More specifically, when the method of the invention is carried out by using the composition for collagen production described in (I) above, a single dose can be suitably adjusted such that the amount of the composition applied to the skin or the like is within the range of 0.5 to 10 mg/cm$^2$.

EXAMPLES

The present invention is described in further detail with reference to Examples and Test Examples. The scope of the invention is not limited to these Examples, however. In the following Test Examples, "w/v %" is a weight (g) per 100 ml unless otherwise specified.

Example 1

Lotion (pH 6.5)

| | |
|---|---|
| Adenosine monophosphate disodium | 3.0 (% by weight) |
| Uridine monophosphate disodium | 0.1 |
| Polyoxyethylene (E.0.60) hardened castor oil | 0.7 |
| Ethanol | 5.0 |
| Glycerin | 2.0 |
| Antiseptic | 0.2 |
| Flavor | Suitable quantity |
| pH adjuster | Suitable quantity |
| Purified water | Balance |
| Total | 100.0% by weight |

A lotion was prepared according to the above formulation in a routine manner.

Example 2

Milky Lotion (pH 6.5)

| | |
|---|---|
| Adenosine monophosphate disodium | 1.5 (% by weight) |
| Uridine monophosphate disodium | 0.01 |
| Carboxyvinyl polymer | 0.3 |
| Decaglyceryl monomyristate | 2.0 |
| Squalane | 5.0 |
| Ethanol | 1.0 |
| Glycerin | 6.0 |
| Antiseptic | 0.2 |
| pH adjuster | Suitable quantity |
| Purified water | Balance |
| Total | 100.0% by weight |

A milky lotion was prepared according to the above formulation in a routine manner.

Example 3

Hair Restorer

| | |
|---|---|
| Adenosine monophosphate disodium | 10.0 (% by weight) |
| Uridine monophosphate disodium | 1.0 |
| Salicylic acid | 0.1 |
| Ethanol | 20.0 |
| Glycerin | 2.0 |
| Antiseptic | 0.2 |
| Flavor | Suitable quantity |
| pH adjuster | Balance |
| Total | 100.0% by weight |

A hair restorer was prepared according to the above formulation in a routine manner.

Example 4

Milky Lotion (pH 6.5)

| | |
|---|---|
| Adenosine monophosphate disodium | 4.0 (% by weight) |
| Uridine monophosphate disodium | 1.0 |
| Carboxyvinyl polymer | 0.3 |
| Decaglyceryl monomyristate | 2.0 |
| Squalane | 5.0 |
| Ethanol | 1.0 |
| Glycerin | 6.0 |
| Antiseptic | 0.2 |
| pH adjuster | Suitable quantity |
| Purified water | Balance |
| Total | 100.0% by weight |

A milky lotion was prepared according to the above formulation in a routine manner.

Test Example 1

Evaluation of the collagen production promoting effect of adenosine monophosphate disodium on cultured human skin fibroblasts.

Primary-cultured human skin fibroblasts (manufactured by Kurabo Industries, Ltd.) were cultured in a 10 cm petri dish, and the cultured cells were collected in the subconfluent state and then freeze-preserved. Using the freeze-preserved cells, an evaluation of the collagen production promoting effect of adenosine monophosphate disodium (hereinafter, referred to as "AMP2Na) was conducted. In the following, the proportion of AMP2Na was based on the concentration of AMP.

<Evaluation Method>

1) The freeze-preserved cells were dissolved in an LSGS (Low Serum Growth Supplement)-containing liquid culture medium 106S (manufactured by Kurabo Industries, Ltd.), and the cell concentration and medium amount were adjusted to 30000 cells/100 μl. 100 μl of thus obtained cell-containing liquid was poured into each well of a test plate.

2) AMP2Na solutions of various concentrations were prepared using a sterilized phosphate buffer solution, and then filtered through a filter, followed by sterilization. The resultants were added to a liquid medium 106S (manufactured by Kurabo Industries, Ltd.) to prepare AMP2Na-containing culture media of various concentrations (0 to $1 \times 10^{-5}$ w/v %).

3) Twenty four hours after injecting cells into the plate wells, it was confirmed that human fibroblasts adhered to the wells, and the medium was removed from each well. Subsequently, an AMP2Na-containing culture medium (200 μl) of one of various concentrations prepared in 2) above was added to each well. The mixtures were cultured at 37° C. under 5% $CO_2$ for two days.

4) Two days after culture initiation, the culture supernatant of each well was collected, and the amount of Procollagen type I C-peptide (PICP) was determined based on the amount of collagen in the culture supernatant using a Procollagen type I C-peptide (PIP) EIA Kit (manufactured by Takara Bio Inc.).

<Results>The results are shown in FIG. 1. As can be seen from FIG. 1, the PICP amount of the cells cultured in the media containing AMP2Na of various concentrations from $1 \times 10^{-8}$ to $1 \times 10^{-5}$ w/v % increased as compared with cells cultured in an AMP-free medium. In particular, it was confirmed that the PICP amount of the cells cultured in the medium containing AMP2Na at a concentration of $1 \times 10^{-5}$ w/v % was about 1.4 times that of the cells cultured in the AMP-free medium.

Test Example 2

Evaluation of the collagen production promoting effect of the combined use of adenosine monophosphate disodium and uridine monophosphate disodium on cultured human skin fibroblasts.

An evaluation of the collagen production promoting effect demonstrated by the combined use of AMP2Na and uridine monophosphate disodium (hereinafter, referred to as "UMP2Na) was conducted. More specifically, media containing AMP2Na and UMP2Na were prepared according to the formulations shown in Table 1 (test media 1 to 4). The evaluation of the collagen production promoting effect of cultured human skin fibroblasts was conducted following the same procedure of Test Example 1 above except for using such media. In Table 1, the proportions of AMP2Na and UMP2Na were based on the concentration of AMP and UMP, respectively.

TABLE 1

| | Proportion (w/v %) | |
|---|---|---|
| | AMP2Na | UMP2NA |
| Test medium 1 | $1 \times 10^{-6}$ | $1 \times 10^{-8}$ |
| Test medium 2 | $1 \times 10^{-6}$ | 0 |
| Test medium 3 | 0 | $1 \times 10^{-8}$ |
| Test medium 4 | 0 | 0 |

Figure 2:
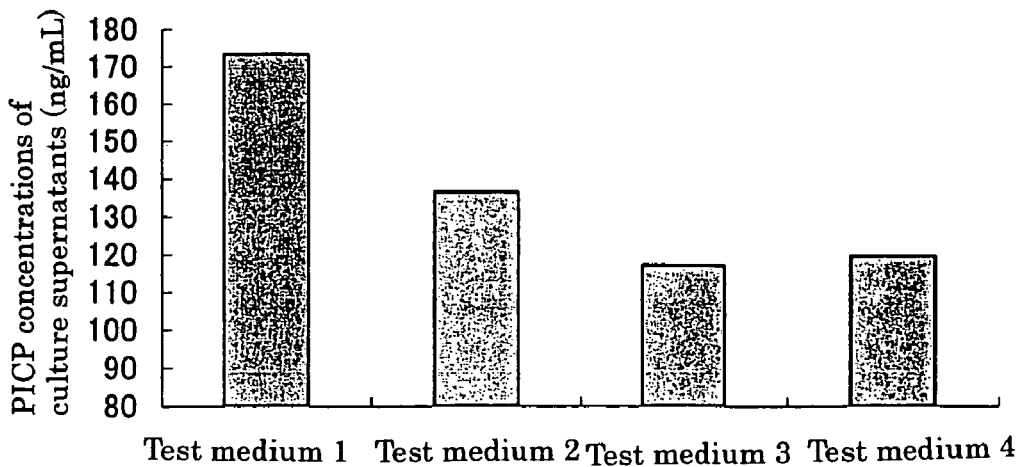
FIG. 2 is a chart showing the PICP concentration produced when the human skin fibroblasts were cultured in media containing various concentrations of AMP2Na and UMP2Na in Test Example 2.

The results are shown in FIG. 2. As can be seen from FIG. 2, AMP2Na has an action of promoting collagen production and UMP2Na sharply potentiates the action of promoting collagen production of AMP2Na, although UMP2Na itself has no action of promoting collagen production.

INDUSTRIAL APPLICABILITY

The purine nucleic acid-related substance contained in the composition for promoting collagen production of the invention as an active ingredient exhibits an excellent action of promoting collagen production. In particular, the action of promoting collagen production of the purine nucleic acid-related substance is potentiated by the co-existence of a pyrimidine nucleic acid-related substance. Accordingly, the composition for promoting collagen production of the invention can be used as an agent for promoting collagen production, and can promote collagen production, and in particular, effectively promote collagen production in the dermis.

Further, the invention provide an externally-applied agent which has an excellent action of promoting collagen production and is useful for anti-aging, moisturizing, anti-acne, anti-wrinkle, anti-sagging, anti-dullness, hair growth, anti-dandruff, nail beautifying, wound healing, etc.

The invention claimed is:

1. A method for promoting collagen production, comprising applying to the skin a composition comprising at least one purine nucleic acid-related substance and at least one pyrimidine nucleic acid-related substance, wherein the purine nucleic acid-related substance is chosen from adenosine phosphate and salts of adenosine phosphate and wherein the pyrimidine nucleic acid-related substance is chosen from uridine monophosphate and salts of uridine monophosphate.

2. A method for promoting collagen production according to claim 1, wherein the purine nucleic acid-related substance is at least one member selected from the group consisting of adenosine monophosphate and a salt thereof.

3. A method for promoting collagen production according to claim 1, wherein the purine nucleic acid-related substance is at least one member selected from the group consisting of adenosine 5'-monophosphate and a salt thereof.

4. A method for promoting collagen production according to claim 1, wherein the pyrimidine nucleic acid-related substance is at least one member selected from the group consisting of uridine 5'-monophosphate and a salt thereof.

5. A method for promoting collagen production according to claim 1, wherein the purine nucleic acid-related substance is selected from the group consisting of adenosine 5'-monophosphate and a salt thereof and the pyrimidine nucleic acid-related substance is at least one member selected from the group consisting of uridine 5'-monophosphate and a salt thereof.

6. A method for promoting collagen production according to claim 1, wherein the composition contains the pyrimidine nucleic acid-related substance in a proportion of 0.001 to 100 parts by weight per part by weight of the purine nucleic acid-related substance.

7. A method for promoting collagen production according to claim 1, wherein the composition contains the purine nucleic acid-related substance in a proportion of 0.01 to 10% by weight based on the total amount of the composition.

8. A method for promoting collagen production according to claim 1, wherein the composition contains the pyrimidine nucleic acid-related substance in a proportion of 0.0001 to 10% by weight based on the total amount of the composition.

* * * * *